United States Patent
Berba et al.

(10) Patent No.: US 6,953,451 B2
(45) Date of Patent: Oct. 11, 2005

(54) THIN COMFORTABLE SANITARY NAPKIN HAVING REDUCED BUNCHING

(75) Inventors: Maria Luisa Berba, Quezon (PH); Stephen John Blanchard, North Brunswick, NJ (US); Michelle Hung Hwa Mar, Castle Hill (AU)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 10/261,319

(22) Filed: Sep. 30, 2002

(65) Prior Publication Data

US 2004/0064120 A1 Apr. 1, 2004

(51) Int. Cl.[7] .............................................. A61F 13/15
(52) U.S. Cl. ................................................. 604/385.01
(58) Field of Search ....................... 604/385.01, 385.03, 604/385.201, 386, 387

(56) References Cited

U.S. PATENT DOCUMENTS

| | | | | |
|---|---|---|---|---|
| 6,312,416 B1 | * | 11/2001 | Brisebois et al. | ...... 604/385.01 |
| 6,440,115 B1 | * | 8/2002 | Connelly et al. | ...... 604/385.14 |
| 6,443,936 B1 | * | 9/2002 | Hamilton et al. | ........... 604/387 |
| 6,503,234 B1 | * | 1/2003 | Canuel et al. | ......... 604/385.01 |
| 6,517,525 B1 | * | 2/2003 | Berthou et al. | ....... 604/385.101 |
| 6,590,135 B1 | * | 7/2003 | Lin | ............................. 604/362 |
| 2001/0007065 A1 | | 7/2001 | Blanchard et al. | |
| 2002/0077618 A1 | * | 6/2002 | Molas | ................. 604/385.201 |
| 2002/0087134 A1 | * | 7/2002 | Drevik et al. | ................ 604/378 |
| 2002/0177832 A1 | * | 11/2002 | Fernandez-Kleinlein et al. | 604/385.01 |
| 2003/0018314 A1 | * | 1/2003 | Nozaki et al. | ........ 604/385.101 |
| 2003/0088222 A1 | * | 5/2003 | Yoshimasa et al. | ......... 604/380 |
| 2003/0088231 A1 | * | 5/2003 | Yoshimasa et al. | ......... 604/387 |
| 2003/0153886 A1 | * | 8/2003 | Lin | ............................. 604/370 |
| 2004/0254556 A1 | * | 12/2004 | Brisebois et al. | ...... 604/385.01 |

FOREIGN PATENT DOCUMENTS

| | | | |
|---|---|---|---|
| EP | 0 940 133 A2 | 9/1999 | |
| EP | 1 206 926 A2 | 5/2002 | |
| EP | 1 078 617 A2 | * 2/2005 | ........... A61F/13/15 |
| WO | WO 95/07674 A2 | 3/1995 | |
| WO | WO 98/51250 A1 | 11/1998 | |

OTHER PUBLICATIONS

European Search Report dated Jan. 22, 2004, for corresponding EP 03022174.1.

* cited by examiner

*Primary Examiner*—Larry I. Schwartz
*Assistant Examiner*—Michael G. Bogart

(57) ABSTRACT

A sanitary napkin for placement in a crotch portion of an undergarment of a wearer having a longitudinal axis and being further characterized by having a preferential bending zone extending obliquely in relation to the longitudinal axis, each preferential bending zone being located solely in an end region and does not extend into a central region of the napkin. The preferential bending zone may be created by mechanically embossing the surface of the sanitary napkin to locally densify the absorbing materials of the article. The preferential bending zone causes the end regions of the sanitary napkin to resist lateral compression forces exerted by the thighs of the wearer and thereby prevents bunching of the article on the undergarment. The central region 70 of the sanitary napkin conforms to the wearer's body providing greater comfort for the wearer of the napkin.

8 Claims, 2 Drawing Sheets

THIN COMFORTABLE SANITARY NAPKIN HAVING REDUCED BUNCHING

FIELD OF THE INVENTION

The present invention relates to a sanitary napkin that is thin, absorbent and has a flexibility selected to provide a good comfort potential and at the same time reduce the likelihood of uncontrolled deformation in use.

BACKGROUND OF THE INVENTION

Recently, the sanitary protection industry has developed improved sanitary napkins that are highly absorbent and at the same time they are thin which significantly enhances their comfort. The conventional wisdom dictates that the comfort of the sanitary napkin is directly related to its flexibility, in particular the flexibility in the lateral direction. Hence, in order to improve the comfort, sanitary napkin designers have almost universally tried to create a product which is as flexible as possible. The idea behind this approach is that the flexible product will create less discomfort to the user particularly when the sanitary napkin is compressed between the thighs of the wearer.

However, sanitary napkins that are highly flexible are known to suffer from high failure rates which can be traced to the inability of the sanitary napkin to maintain firm contact with the user's body. As a consequence, the menstrual liquid discharged cannot be captured immediately into the sanitary napkin and liquid can travel along the user's body and stain the user's undergarments or outer garments. Studies have demonstrated that sanitary napkins that are highly flexible, when placed in the crotch portion of the user and compressed by the user's thighs, deform laterally according to a random or uncontrolled manner. This results into the so-called "bunching" problem. A sanitary napkin that bunches is compressed in a way to significantly reduce its liquid absorption area and prevent close conformation with the vaginal opening. This may explain the high incidence of failure rates observed in connection with sanitary napkins that are very flexible.

One possible manner to increase the lateral rigidity of a sanitary napkin that is taught by the prior art is to calendar the napkin between a pair of rolls. This operation stiffens the entire product by the effect of compaction. A drawback of this operation, however, is to negatively affect the absorption capacity of the sanitary napkin. The compaction effectively reduces the amount of void volume in the absorptive layers of the sanitary napkin, thus reducing its ability to store liquid.

Thus, there exists in the industry a need to provide a sanitary napkin that is thin, highly absorbent and has good comfort potential and at the same time is capable of reducing the incidence of bunching in use.

SUMMARY OF THE INVENTION

In accordance with the present invention, there has been provided sanitary napkin adapted to be worn in a crotch portion of an undergarment of a wearer, said sanitary napkin having a main body including a liquid permeable cover layer, a liquid impermeable barrier layer and an absorbent core intermediate the cover layer and barrier layer, the main body having two longitudinal side edges defining therebetween a width and two spaced apart transverse ends defining therebetween a length, an imaginary central longitudinal axis that bisects the main body into two substantially equal halves, a transverse axis that is perpendicular to the longitudinal axis, a first end region, an opposite second end region and a central region intermediate the first and second end regions, the first end region and the second end region each having a respective preferential bending zone extending obliquely in relation to the longitudinal axis, said preferential bending zone extending from one longitudinal side area of the sanitary napkin to an opposite longitudinal side area and crossing the central longitudinal axis of the sanitary napkin, wherein each preferential bending zone is located solely in a respective end region and does not extend into the central region.

Other embodiments and features of the present invention will become apparent to those ordinarily skilled in the art upon review of the following description of specific embodiments of the invention in conjunction with the accompanying drawings.

DETAILED DESCRIPTION

Figure 1:
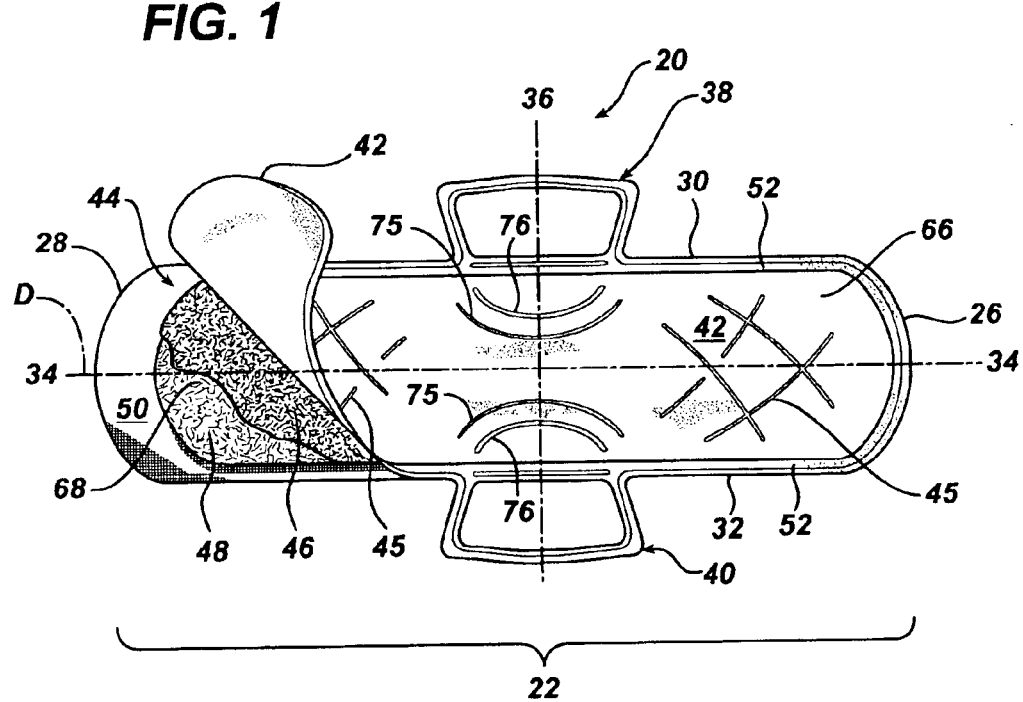
FIG. 1 is a top elevational view of a sanitary napkin in accordance with the present invention.

Referring to FIG. 1 there is shown an embodiment of the present invention, a feminine sanitary napkin 20. The sanitary napkin 20 has a main body 22 with a first transverse end 26 and an opposite second transverse end 28 defining therebetween a length. The main body 22 also has two longitudinal sides, namely a longitudinal side edge 30 and an opposite longitudinal side edge 32 defining therebetween a width. The main body 22 has a central longitudinal axis 34 that is an imaginary line bisecting the sanitary napkin 20 in two substantially identical halves. The main body 22 also has an imaginary transverse centerline 36 perpendicular to the central longitudinal axis 34.

Figure 2:
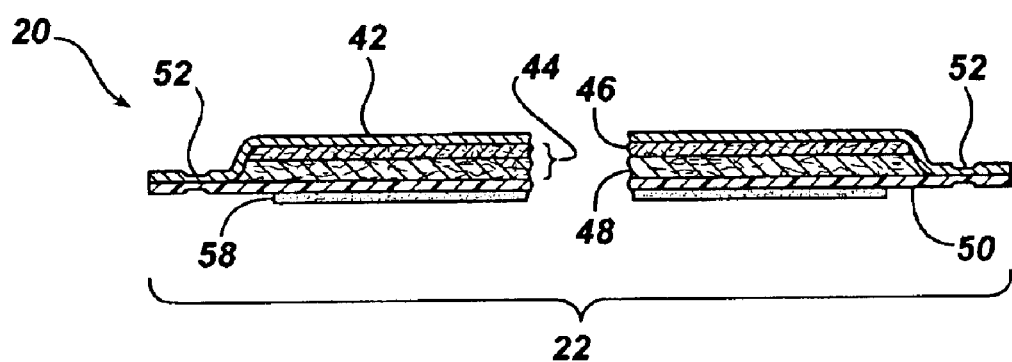
FIG. 2 is a cross-sectional view taken along the longitudinal axis of the sanitary napkin shown in FIG. 1.

As depicted in FIG. 2, which is a cross sectional view of the sanitary napkin 20 in FIG. 1, the main body 22 is of a laminate construction and preferably comprises a liquid permeable cover layer 42, an absorbent core 44, and a liquid impervious barrier layer 50. The absorbent core 44 may comprise a single layer, or alternatively, the absorbent core 44 preferably has two components as shown, including a first absorbent layer 46 and a second absorbent layer 48. The first absorbent layer 46 is adapted to rapidly acquire liquid from the cover layer 42 and to hold the liquid until the second absorbent layer 48 can absorb and retain the absorbed liquid. When the absorbent core 44 comprises a single layer, it is preferably the second absorbent layer 48 as described hereinbelow.

In accordance with the present invention, a preferential bending zone 45 is included in each of the transverse end regions 66, 68 of the sanitary napkin 20. The preferential bending zones 45 are located solely in the transverse end regions 66, 68 of the sanitary napkin 20 and there are no preferential bending zones located in the central region 70 of the sanitary napkin. The terminology "central region" of the sanitary napkin, as used herein is that region of the sanitary napkin that registers with the vaginal opening of the user when the sanitary napkin is worn. The transverse end regions 66, 68, accordingly, are the regions of the sanitary napkin that are intermediate the first and second transverse ends 26, 28 of the napkin 20 and the central region 70, respectively. It has been discovered that when the sanitary napkin 20 is provided with a preferential bending zone 45 in each transverse end region 66, 68 of the main body 22 of the sanitary napkin 20 that extends obliquely with respect to the longitudinal axis 34 of the napkin, the effect is to stiffen the napkin in both a lateral and longitudinal direction by virtue of it orientation with relation to the longitudinal axis and thus enhance the napkin's ability to resist bunching. The result is an engineered rigidity that creates resistance to lateral compression in the transverse end regions 66, 68 of the sanitary napkin 20 and at the same time does not make the napkin overly stiff. Advantageously, the transverse end regions 66, 68 of the sanitary napkin 20 are able to independently twist along their respective longitudinal axes while allowing the central region 70 to adapt to the contours of the wearer's body and thereby allow the sanitary napkin conform to the shape of the wearer's body, providing the sanitary napkin with enhanced comfort and stability in use.

Referring again to FIG. 1, the main body 22 of the sanitary napkin 20 is provided with a preferential bending zone 45 in each transverse end region of the sanitary napkin. In a preferred embodiment, the preferential bending zone 45 crosses the longitudinal axis of the sanitary napkin. This obliquely extending preferential bending zone 45 extends from one longitudinal side area of the sanitary napkin 20 to the opposite longitudinal side area, crossing the imaginary central longitudinal axis 34 of the sanitary napkin 20. The obliqueness requirement of the preferential bending zone 45 is met as long as a substantial segment of the preferential bending zone 45 is oblique with relation to the central longitudinal axis 34. Thus, even when only one or more parts of the preferential bending zone 45 are oblique with relation to the central longitudinal axis 34 and other parts are not oblique, the obliqueness requirement is still met as long as the oblique portions provide a bending axis that is oblique with respect to the central longitudinal axis. Preferably, the segment of the preferential bending zone 45 that is oblique represents at least 25% of the length of the preferential bending zone 45, more preferably 50% and most preferably 100% of the length of the preferential bending zone 45. Preferably, the segment that is oblique crosses the longitudinal axis. A preferred method of creating the preferential bending zones is to mechanically emboss the surface of the main body of the sanitary napkin, resulting in a series of local densifications of the absorbent material. An advantage afforded by forming the oblique preferential bending zones as embossed channels is that they contribute to a more uniform distribution of bodily fluids along the surface of the sanitary napkin by channeling the fluids away from the point of contact. The sanitary napkin is also more efficient in collecting bodily fluids, since a larger surface area is available for contact with the fluids than when bunching occurs.

The preferential bending zone 45 can be straight, arcuate, form a repeating pattern, such as a wavy pattern or a zigzag pattern or a combination of these shapes. When a repeating pattern is present in a segment of the preferential bending zone 45, the obliqueness of that segment is determined by considering an imaginary line that is contained within the repeating pattern and that either forms or at least approximates a line of symmetry for the pattern. The transverse ends of the sanitary napkin may be provided with a plurality of preferential bending zones in a variety of patterns, including a plurality of substantially parallel lines, a plurality of parallel and converging lines, etc. In a preferred embodiment, when the plurality of preferential bending zones are in the form of parallel lines, the spacing between the parallel lines is about 2 cm. In preferred embodiment, the sanitary napkin 20 has a plurality of preferential bending zones that converge towards a common point of intersection to create the appearance of a "basket weave" type pattern extending over a major portion of the longitudinal dimension of the transverse end regions of the main body of the sanitary napkin. In accordance with this preferred embodiment of the invention, the sanitary napkin has a plurality of obliquely extending preferential bending zones 45 that are disposed across the surface of the transverse end regions 66, 68 of the main body 22 of the sanitary napkin 20 wherein adjacent preferential bending zones converge towards each other. Under this embodiment, the oblique preferential bending zones are arcuate.

The preferential bending zone 45 may optionally intersect with another adjacent preferential bending zone 45 in the basket weave pattern. The preferential bending zones are preferably oblique over 100% of their length with relation to the longitudinal axis and more preferably they are arcuate along a substantial portion of their length. In a variant the oblique preferential bending zones could also be straight or form a repeating pattern, such as a wavy pattern or a zigzag pattern. The oblique preferential bending zones may be created in one or more of the cover layer 42, absorbent core 44 or the barrier layer 50. In a preferred embodiment, the preferential bending zones are created in the cover layer 42 and absorbent core 44. Each preferential bending zone 45 extends generally along an angle of 45 degrees with respect to the longitudinal axis or lateral axis of the main body of the sanitary napkin. The pattern is designed such that each preferential bending zone 45 intersects at least two other preferential bending zones. Also, each preferential bending zone 45 extends from one longitudinal side area of the sanitary napkin to the opposite longitudinal side area, crossing the imaginary longitudinal axis of the sanitary napkin. A longitudinal side area is defined as a portion of the sanitary napkin that extends inwardly from and includes a respective longitudinal side edge 30, 32, the side edge forming the outer boundary of the side area. Each side area has a width that is about 25% of the maximal transverse dimension of the sanitary napkin 20. This dimension is measured without taking into account the flaps. It is the maximal distance defined between the longitudinal side edges 30, 32 of the sanitary napkin 20. It is preferred that the preferential bending zone 45 does not extend to the longitudinal sides of the sanitary napkin and are spaced inward from each side edge by at least 2 mm, preferably spaced inward by at least 5 mm. In a most preferred embodiment, the preferential bending zone 45 is spaced inward from the longitudinal side edges of the absorbent core 44.

In an alternative embodiment, the preferential bending zones are created in the absorbent core 44 only, so that they are less visible on the sanitary napkin than when the preferential bending zones are made on the cover layer 42 and absorbent core 44.

In accordance with another embodiment of the present invention, the central region 70 is provided with a longitudinally extending hinge adjacent to and inward from each longitudinal side edge of the sanitary napkin. It is important to note that the longitudinally extending hinges in the central region 70 of the sanitary napkin 20 are distinct from the preferential bending zones 45 in the transverse end regions of the napkin in that the longitudinally extending hinges do not extend obliquely across the central longitudinal axis 34. Rather, the longitudinally extending hinges extend longitudinally adjacent the longitudinal side edges 30, 32, respectively. Thus, while the longitudinally extending hinges may optionally have obliquely extending portions, these portions do not cross the central longitudinal axis. It is preferred that no portion of the longitudinally extending hinge cross the central longitudinal axis 34.

In a more preferred embodiment, the central region 70 is provided with two longitudinally extending hinges. The longitudinally extending hinges are located substantially within the central region 70 adjacent each respective longitudinal edge, each hinge being adapted to provide a longitudinally extending preferential bending axis. The hinges are spaced apart along at least a portion of their length. It is preferred that at least one hinge has a radius of curvature and an adjacent hinge is substantially straight. As shown in FIG. 1 a first hinge 75 has a radius of curvature and is closer to the central longitudinal axis 34 than the second hinge 76 that is substantially straight.

Alternatively, the first hinge may be substantially straight (not shown) and is closer to the central longitudinal axis 34 than the second hinge 76 that has a radius of curvature. The first hinge 75 is generally separated from the second hinge 76 along a substantial portion of their respective lengths but may optionally be co-terminus and also may optionally contact one another at their respective distal ends.

In a preferred embodiment, each hinge has a radius of curvature and preferably one hinge has a radius of curvature greater than an adjacent hinge. The first hinge 75, which is closer to the central longitudinal axis 34 than the second hinge 76, may have a lower radius of curvature than the second hinge. Alternatively, the first hinge 75 may have a greater radius of curvature than the second hinge 76.

In any of the foregoing embodiments, it has been found that by providing a sanitary napkin with at least two substantially centrally located longitudinal hinges adjacent each longitudinal side edge of the main body, wherein one hinge has a greater radius of curvature than the adjacent hinge provides an optimum fit to a wide variety of wearers' anatomies. That is the multiple longitudinal hinges create a sanitary napkin that has multiple modes of controlled deformation that enables the napkin to conform to the entire range of user anatomies. Moreover, the multiple longitudinal hinges control bunching rather than prevent bunching to create greater comfort, fit to the anatomy and discretion.

The combination of multiple hinges with differences in curvature provides a controlled deformation in an enhanced manner. A hinge having a lower radius of curvature (less straight) has more lateral stability than a hinge having a higher radius of curvature (more straight) since it has more lateral components and can thus resist transverse compression. The hinge with a higher radius of curvature will have a greater tendency to bend relative to a hinge with a lower radius of curvature. Thus the hinge with the lower radius of curvature has a greater resistance to bunching and will maintain the napkin is a flatter (i.e. more planar) configuration in use. The combination of these two hinge types along each longitudinal side of the main body enables the main body to conform to a wide range of user anatomies.

Longitudinally extending hinges 75, 76 may include any material in an amount sufficient to impart additional structural rigidity relative to adjacent regions. Examples of suitable material to form the longitudinally extending hinges 75, 76 comprise a sphagnum-moss containing insert, a densified channel, strips of polymeric foam, and the like and combinations thereof. In a preferred embodiment, each longitudinally extending hinge 75, 76 is created by compressing, embossing or scoring one or more layers of the absorbent structure in an amount sufficient to create a longitudinally extending preferential bending line. When the longitudinally extending hinges 75, 76 comprise a densified channels, they are preferably located between the central longitudinal axis and the longitudinal edge. Densified side channels may be formed in the main body by heating and compressing the cover layer/absorbent element/barrier layer assembly in selected areas to form densified channels similar to those shown in FIG. 1. The density of the channels is at least two times the density of the adjacent non-densified regions and is preferably from two to ten times the density of the adjacent regions of the absorbent core. The density of the channels is preferably at least 0.5 g/cc. The longitudinally extending hinges 75, 76 are adapted to maintain the central region 70 of the main body portion in a relatively flat profile along the longitudinal axis and resists bending transverse to that axis. A central region 70 having a longitudinally extending hinges 75, 76 has been found to effectively conform to the body in that region, resist asymmetrical deformation due to the application of laterally compressive forces and thereby prevents leakage of liquid from the main body portion. That is, since the hinges effectively control deformation, when subjected to laterally compressive forces of a user's thighs, the sanitary napkin will deform symmetrically about the central longitudinal axis rather than deforming randomly across its width.

The cover layer 42 may be any soft, flexible material that is liquid permeable and is capable of rapidly absorbing body liquid and transporting it away from the body and the point of deposition. In a preferred embodiment, the cover layer 42 is a relatively low density, bulky, high-loft non-woven web material. The non-woven web material may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Bi-component fibers may be made up of a polyester core and a polyethylene sheath. The use of appropriate bi-component materials results in a fusible non-woven fabric. Using a fusible fabric increases the ease with which the cover layer 42 may be mounted to the adjacent first absorbent layer and/or to the barrier layer 50.

The cover layer 42 preferably has a relatively high degree of wettability, although the individual fibers comprising the cover may not be particularly hydrophilic. Advantageously, the fibers which make up the cover layer 42 should not lose their physical properties when they are wetted, in other words they should not collapse or lose their resiliency when subjected to water or body liquid. The cover layer 42 may be treated to allow liquid to pass through it readily. The cover layer 42 also functions to transfer the liquid quickly to the other layers of the absorbent core 44. Thus, the cover layer 42 is advantageously wettable, hydrophilic and porous. When composed of synthetic hydrophobic fibers such as polypropylene or bi-component fibers, the cover layer 42 may be treated with a surfactant to impart the desired degree of wettability.

Alternatively, the cover layer 42 can also be made of an apertured polymer film wherein the apertures form large pores that are capable of quickly transferring body liquid to the inner layers of the absorbent core. The film may be a single layer film such as polyethylene or polypropylene film or alternatively may be formed as a multi-layered co-extruded film. Suitable apertured films that are suitable for use in the present invention are well known to those skilled in the art.

The cover layer 42 may be affixed to the remainder of the absorbent core 44 in order to aid in promoting liquid transport by fusing the cover to the subjacent layer. Such affixation may be effected locally, at a plurality of sites or over the entire contact surface of cover layer 42 with absorbent core 44 using such techniques as adhesive, embossing, heat-bonding, ultrasonic bonding, and the like.

Adjacent to the cover layer 42 on its inner side and bonded to the cover layer 42 is a first absorbent layer 46 that forms part of the absorbent core 44. The first absorbent layer 46 provides the means of receiving body liquid from the cover layer 42 and holding it until an underlying second absorbent layer has an opportunity to absorb the liquid.

The first absorbent layer 46 is, preferably, more dense than and has a larger proportion of smaller pores than the cover layer 42. These attributes allow the first absorbent layer 46 to contain body liquid and hold it away from the outer side of the cover layer 42, thereby preventing the liquid from re-wetting the cover layer 42 and its surface. However, the first absorbent layer 46 is, preferably, not so dense as to prevent the passage of the liquid through the layer 46 into the underlying second absorbent layer 48. These types of absorbent layers are commonly known as liquid transfer layers or acquisition layers.

The first absorbent layer 46 may be composed of fibrous materials, such as wood pulp, polyester, rayon, polypropylene, polyethylene, or the like, or combinations thereof. The first absorbent layer 46 preferably comprises thermoplastic fibers that are thermobonded together for the purpose of stabilizing the layer and maintaining its structural integrity. The first absorbent layer 46 may be treated with surfactant on one or both sides in order to increase its wettability, although generally the first absorbent layer 46 is relatively hydrophilic and may not require treatment. The first absorbent layer 46 is preferably bonded on both sides to the adjacent layers, i.e. the cover layer 42 and an underlying second absorbent layer 48.

Immediately subjacent to and bonded to the first absorbent layer 46 is the second absorbent layer 48. In a preferred embodiment, the first absorbent layer 46 has a central width that is at least about the same as the central width of the second absorbent layer 48. In another embodiment, the first absorbent layer 46 has a central width that exceeds the central width of the second absorbent layer 48. The term "central width" refers to a specific area of a layer, such as an absorbent layer determinable as follows. A reference point on the sample layer that is disposed beneath the center of the vaginal orifice, when worn, is located. A plane parallel to the transverse centerline 36 and 3.75 centimeters forward from the reference point in the direction of the wearer's mons pubis is located. Another plane parallel to the lateral centerline 36 and 5.0 centimeters rearward from the reference point in the direction of the wearer's buttocks is also located. The greatest flat-out, uncompressed, unmanipulated, lateral width of the sample layer between the two planes is the absorbent width of the sample layer. In a preferred embodiment, the central width of the first absorbent layer 46 is greater than about 64 mm. The central width of the absorbent core, when the absorbent core includes a plurality of absorbent layers is the central width of the layer of the absorbent core that has the largest central width.

In a preferred embodiment, the second absorbent layer 48 is a blend or mixture of cellulosic fibers and superabsorbent polymer particles. For the purposes of the present invention, the term "superabsorbent polymer" or "superabsorbent particle" (both terms being commonly used interchangeably are hereinafter referred to as "SAP") refers to materials which are capable of absorbing and retaining at least about 10 times their weight in body liquids under a 0.5 psi pressure.

Suitable SAP for use in the present invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers.

In a specific example, the second absorbent layer 48 is a material containing from about 40 weight percent to about 95 weight percent cellulosic fibers; and from about 5 weight percent to about 60 weight percent SAP. The material has a water content of less than about 10 weight percent. As used herein, the phrase "weight percent" means weight of substance per weight of final material. By way of example, 10 weight percent SAP means 10 g/m$^2$ SAP per 100 g/m$^2$ basis weight of the material.

Cellulosic fibers that can be used in the second absorbent layer 48 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

In a specific example the second absorbent layer 48 is a material containing from about 50 to about 95 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

The second absorbent layer 48 can be manufactured by using air-laying means well known in the art. Cellulosic fibers (e.g., wood pulp fibers) are processed using a hammer mill to individualize the fibers. The individualized fibers may be blended with SAP granules in a blending core and pneumatically conveyed into a series of forming heads. The blending and distribution of fibers and SAP granules can be controlled separately for each forming head. Fibers (and SAP) from each forming chamber are deposited by vacuum onto a forming surface thus forming a layered absorbent web. The web is subsequently compressed using calenders to achieve desirable density. The densified web is wound into a roll using conventional winding equipment. The forming surface may be covered with tissue paper to reduce the loss of material. The tissue paper layer can be removed prior to calendering or incorporated into the formed material. In a possible variant, the first absorbent layer 46 can be formed integrally with the second absorbent layer 48 to provide a unitized absorbent core 44.

The second absorbent layer 48 of the present invention is of high density and in a specific example has a density of greater than about 0.25 g/cc. Specifically, the second absorbent layer 48 may have a density in the range of from about 0.30 g/cc to about 0.50 g/cc. More specifically, the density is from about 0.30 g/cc to about 0.45 g/cc and, even more specifically from about 0.35 g/cc to about 0.40 g/cc.

Air-laid absorbents are typically produced with a low density. To achieve higher density levels, such as the examples of the second absorbent layer 48 given above, the air-laid material is compacted using calenders as is well known in the art. Typically such compacting is carried out at a temperature of about 100 degrees C. and a load of about 130 Newtons per millimeter. In one embodiment the second absorbent layer 48 has a ratio of Gurley stiffness, measured in milligrams (mg) to density, measured in grams per cubic centimeter (g/cc), of less than about 3700. In a specific example, that ratio of Gurley stiffness to density is less than about 3200 and, more specifically, less than about 3000.

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171 E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams.

The second absorbent layer 48 is strong in light of its softness. Pad integrity is a well-known measurement of absorbent material strength. In a specific embodiment the second absorbent layer 48 demonstrates strength (high pad integrity) over a wide range of densities. In a specific example the second absorbent layer 48 has a pad integrity, measured in Newtons (N), to density (g/cc) ratio of greater than about 25.0. In a more specific example, that ratio is greater than about 30.0 and, could even be greater than about 35.0. The pad integrity is a test performed on an Instron Universal Testing Machine. Essentially, the test measures the load required to pierce through the test sample, as described in the PFI Method of 1981. A test sample having dimensions of 50 mm by 50 mm is clamped on the Instron with a suitable fastening device. A 20 mm diameter piston traveling at the rate of 50 mm/min punctures the stationary sample. The force required to puncture the sample is measured in Newtons (N).

The second absorbent layer 48 has a basis weight in the range of from about 100 $g/m^2$ to about 700 $g/m^2$. In a specific example, the basis weight ranges from about 150 $g/m^2$ to about 350 $g/m^2$. Preferably the basis weight ranges from about 200 $g/m^2$ to about 300 $g/m^2$ and, more preferably, to about 250 $g/m^2$.

The second absorbent layer 48 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

The second absorbent layer 48 has a thickness that varies from about 0.5 mm to about 2.5 mm. In a preferred embodiment, the thickness is from about 1.0 mm to about 2.0 mm and, even more preferably from about 1.25 mm to about 1.75 mm.

One embodiment of the second absorbent layer 48 particularly well suited for use in the sanitary napkin 20 is depicted in FIG. 6. Such second absorbent layer 48 has a basis weight of from about 200 $g/m^2$ to about 350 $g/m^2$ and a density between about 0.3 g/cc and 0.5 g/cc. In a specific example, the density is from about 0.3 g/cc to about 0.45 g/cc and, more specifically about 0.3 g/cc to about 0.4 g/cc.

The second absorbent layer 48 may be air-laid as three strata: a bottom layer of pulp (without superabsorbent) with a basis weight of about 25 $g/m^2$; a middle layer with a basis weight of about 150 $g/m^2$ and which contains from about 10 to about 30 $g/m^2$ superabsorbent and from about 120 $g/m^2$ to about 140 g $m^2$ pulp; and a top layer of pulp (without superabsorbent) with a basis weight of about 25 $g/m^2$. Relative to the total basis weight of the second absorbent layer 48, the level of superabsorbent ranges from about 5 to about 15 weight percent ($g/m^2$ of superabsorbent per $g/m^2$ material). In a specific example, the level of superabsorbent is from about 7.5 weight percent to about 12.5 weight percent of the material. More specifically, the material contains about 10 weight percent of superabsorbent. Thus, the middle layer of the material could contain from about 15 $g/m^2$ to about 25 $g/m^2$ superabsorbent and from about 125 $g/m^2$ to about 135 $g/m^2$ pulp and, more specifically about 20 $g/m^2$ superabsorbent and about 130 $g/m^2$ pulp. The middle layer containing pulp and superabsorbent can be laid down as a homogeneous blend or as a heterogeneous blend wherein the level of superabsorbent varies with proximity to the bottom layer.

In another embodiment, the second absorbent layer 48 may be air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 $g/m^2$ superabsorbent and from about 40 g $m^2$ to about 65 $g/m^2$ pulp. When it is desired to keep absorbed liquid away from the cover layer 42 the amount of superabsorbent in the first and second middle layers is adjusted such that there is a higher level of superabsorbent in the second middle layer. The superabsorbent in the first and second middle layers can be the same or a different superabsorbent.

Underlying the absorbent core 44 is a liquid impermeable barrier layer 50 comprising liquid-impervious film material so as to prevent liquid that is entrapped in the absorbent core 44 from egressing the sanitary napkin and staining the wearer's undergarment. The barrier layer 50 is made preferably of polymeric film.

The cover layer 42 and the barrier layer 50 are joined along their marginal portions so as to form an enclosure or flange seal that maintains the absorbent core 44 captive. The flange seal may be made by means of adhesives, heat-bonding, ultrasonic bonding, radio frequency sealing, mechanical crimping, and the like and combinations thereof. The peripheral seal line is shown in FIG. 1 by the reference numeral 52.

The sanitary napkin 20, as shown in FIG. 1 has two flaps 38, 40 that project laterally outward, one flap extending from each of the longitudinal sides 30, 32. The flaps 38, 40 are preferably in the shape of an isosceles trapezoid with the top adjoining the longitudinal side and the base at the distal end. This is an example only as other flap shapes can also be used without departing from the spirit of the invention. The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent core 44. Alternatively, the flaps may include absorbent material between the cover layer 42 and the barrier layer 50 extensions. Such absorbent material may be an extension of the first absorbent layer 46, the second absorbent layer 48 or both.

Referring to FIG. 2, in order to enhance the stability of the sanitary napkin, the garment facing surface of the barrier layer 50 is provided with positioning adhesive material 58, typically hot-melt adhesive material capable of establishing a temporary bond with the undergarment material. A suitable material is the composition designated HL-1491 XZP commercially available from H. B. Fuller Canada, Toronto, Ontario, Canada. The positioning adhesive 58 may be applied to the garment-facing surface of the barrier layer 50 in various patterns, including complete adhesive coverage, parallel longitudinal lines, a line of adhesive following the perimeter of the structure, transverse lines of adhesive or the like.

Standard release paper (not shown) covers the positioning adhesive 58 before the napkin is used to prevent the unwanted adherence of the napkin to itself or foreign objects. The release paper is of conventional construction (e.g. silicone coated wet-laid Kraft wood pulp).

The main body 22 of the sanitary napkin 20 has an average thickness that is generally less than about 5 mm, preferably less than 3 mm and more preferably is less than 2 mm. In a particularly preferred embodiment, the main body 22 of the sanitary napkin 20 has a thickness of about 2.8 mm.

An apparatus that is suitable to measure the thickness of the sanitary napkin is a footed dial (thickness) gauge with stand, available from Ames, with a 2" diameter foot and a readout accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are not considered when taking the thickness reading of the sample.

The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. A load of 0.07 p.s.i.g. is applied to the sample and the read out is allowed to stabilize for approximately 5 seconds. The thickness reading is then taken. The thickness of the release paper covering the positioning adhesive is deducted from the total thickness.

The flexural resistance of the sanitary napkin is preferably in the range from about 200 g to about 800 g. The flexural resistance of a sanitary napkin is measured by peak bending stiffness. Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform which is 102.0 mm by 102.0 by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;
3. A force-measurement gauge and more specifically an Instron inverted compression load cell. The load cell has a load range of from about 0.0 to about 2000.0 g;
4. An actuator and more specifically the Instron Model No. 1122 having an inverted compression load cell. The Instron 1122 is made by the Instron Engineering Corporation, Canton, Mass.

In order to perform the procedure for this test, as explained below, five representative sanitary napkins are necessary. From one of the five napkins to be tested, some number "Y" of 37.5 mm by 37.5 mm test specimens are cut. Specimens having portions in which a cover layer is joined directly to a barrier layer or which are a laminate of a cover layer, and a barrier layer without any component of the absorbent core, should not be tested. This test is more concerned with the overall flexibility of the sanitary napkin and not merely the peripheral portions thereof and, therefore, the flexibility of the present invention is more concerned with the flexibility of the absorbent portions of the sanitary napkin.

The test specimens should not be folded or bent by the test person, and the handling of specimens must be kept to a minimum and to the edges to avoid affecting flexural-resistance properties. From the four remaining sanitary napkins, an equal number "Y" of 37.5 mm by 37.5 mm specimens, identical to the specimens cut from the first napkin, are cut. Thus, the test person should have "Y" number of sets of five identical specimens.

The procedure for the CIRCULAR BEND PROCEDURE is as follows. The specimens are conditioned by leaving them in a room that is 21 degree Celsius plus or minus 1 degree Celsius. and 50% plus or minus 2.0% relative humidity for a period of two hours. The test plate is leveled. The plunger speed is set at 50.0 cm per minute per full stroke length. A specimen is centered on the orifice platform below the plunger such that the cover layer of the specimen is facing the plunger and the barrier layer of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the "Y" sets tested. The flexural resistance for a sanitary napkin is the greatest of the average peak bending stiffness.

The above-described embodiment of the sanitary napkin 20 may be fabricated in a conventional manner in accordance with conventional techniques. Specifically, a laminate structure comprising the following layers of material in a top-to-bottom order: a cover layer material; an absorbent layer material; a second absorbent layer material (manufactured as described above); and finally a barrier layer material. Some of the materials are necessarily not continuous within the laminate structure, and where such is the case, they are positioned precisely, one with respect to another, in the relationship they will occupy in the final products. The cover layer material and the barrier layer material are then bonded together by applying pressure, optionally in combination with adhesive, in the appropriate positions, and what will become the peripheral seal is created. The sealed structure is then severed by conventional means (i.e. die-cutting, liquid-jet cutting, or by laser) from the web to create a discrete article.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A sanitary napkin adapted to be worn in a crotch portion of an undergarment of a wearer, said sanitary napkin having a main body including a liquid permeable cover layer, a liquid impermeable barrier layer and an absorbent core intermediate the cover layer and barrier layer, the main body having two longitudinal side edges defining therebetween a width and two spaced apart transverse ends defining therebetween a length, an imaginary central longitudinal axis that bisects the main body into two substantially equal halves, a transverse axis that is perpendicular to the longitudinal axis, a first end region, an opposite second end region and a central region intermediate the first and second end regions, the first end region and the second end region each having a respective preferential bending zone extending obliquely in relation to the longitudinal axis, said preferential bending zone extending from one longitudinal side area of the sanitary napkin to an opposite longitudinal side area and crossing the central longitudinal axis of the sanitary napkin, wherein each preferential bending zone is located solely in a respective end region and does not extend into the central region, wherein said preferential bending zone is arcuate.

2. A sanitary napkin as defined in claim 1, wherein said sanitary napkin has a thickness less than about 5 mm.

3. A sanitary napkin according to claim 1, wherein said first end region and said second end region each comprise a plurality of preferential bending zones spaced apart from one another.

4. A sanitary napkin according to claim 3, wherein said preferential bending zones intersect each other.

5. A sanitary napkin according to claim 1, wherein the central region has a pair of spaced apart longitudinally extending hinges, one hinge being adjacent to and inward from each longitudinal side edge.

6. A sanitary napkin according to claim 1, wherein the central region has two pairs of spaced apart longitudinally extending embossed hinges, one pair of hinges being adjacent to and inward from each longitudinal side edge.

7. A sanitary napkin according to claim 5, wherein said preferential bending zone and said hinges are embossed channels which compresses said absorbent core.

8. A sanitary napkin according to claim 1, wherein said preferential bending zone is an embossed channel which compresses said liquid permeable cover layer and said absorbent core.

* * * * *